United States Patent [19]
Mogg

[11] Patent Number: 5,690,616
[45] Date of Patent: Nov. 25, 1997

[54] CATHETER CLAMP

[76] Inventor: Alan David Mogg, 44 Albert Road, Ferndown, Dorset, BH22 9HE, England

[21] Appl. No.: 588,011

[22] Filed: Jan. 16, 1996

[51] Int. Cl.$^6$ ................................................ A61M 25/02
[52] U.S. Cl. .................. 604/174; 604/180; 128/DIG. 26
[58] Field of Search ........................ 604/174, 176–180; 128/DIG. 26

[56] References Cited

U.S. PATENT DOCUMENTS

| | | | |
|---|---|---|---|
| 4,193,174 | 3/1980 | Stephens | 128/DIG. 26 X |
| 4,261,363 | 4/1981 | Russo | 128/350 R |
| 4,360,025 | 11/1982 | Edwards | 604/180 |
| 4,397,647 | 8/1983 | Gordon | 604/180 |
| 4,419,094 | 12/1983 | Patel | 604/93 |
| 4,517,971 | 5/1985 | Sorbonne | 604/174 X |
| 4,533,349 | 8/1985 | Bark | 604/174 |
| 4,645,492 | 2/1987 | Weeks | 604/174 |
| 4,659,329 | 4/1987 | Annis | 604/180 |
| 4,976,698 | 12/1990 | Stokley | 604/174 |
| 5,116,324 | 5/1992 | Brierley et al. | 604/180 |
| 5,342,324 | 8/1994 | Tucker | 604/174 X |
| 5,370,627 | 12/1994 | Conway | 604/180 |

FOREIGN PATENT DOCUMENTS

| | | |
|---|---|---|
| 0327299 | 8/1989 | European Pat. Off. . |
| 2147811 | 8/1984 | United Kingdom . |
| WO 9107204 A2 | 5/1991 | WIPO . |

*Primary Examiner*—Sam Rimell
*Assistant Examiner*—Robert V. Racunas
*Attorney, Agent, or Firm*—Reinhart, Boerner, Van Deuren Norris & Rieselbach, s.c.

[57] ABSTRACT

A catheter clamp comprises a base (1) for securing by adhesion to the skin, a hole (2) in the base for passage of a catheter tube (3), a curved tube support surface (14) for supporting the tube which is bent in use through about 90°, and an arm (6) pivoted at (8) between parallel upstanding side walls (4) on the base. The arm (6) has a curved portion (22) extending eccentrically of the pivot (8) which urges a tube portion (23) above the hole (2) into a vertical channel provided in a post (12), and grips the tube when the arm is pivoted to an operative clamping position. The arm is held by retention means (24, 25) in the clamping position. In another embodiment (FIGS. 8, 9) the manually operable clamping means is provided by a slider (50).

20 Claims, 7 Drawing Sheets

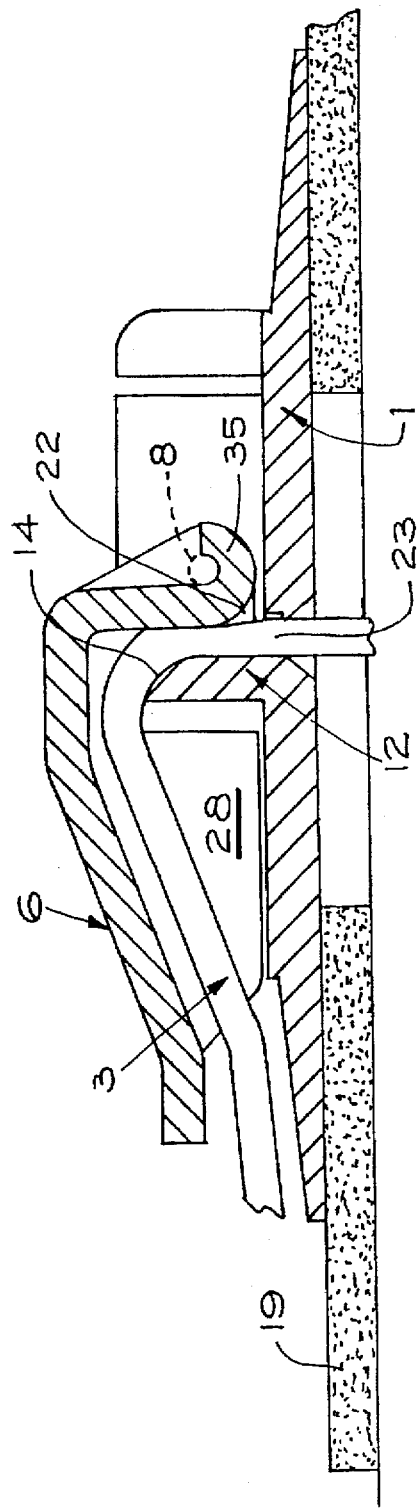
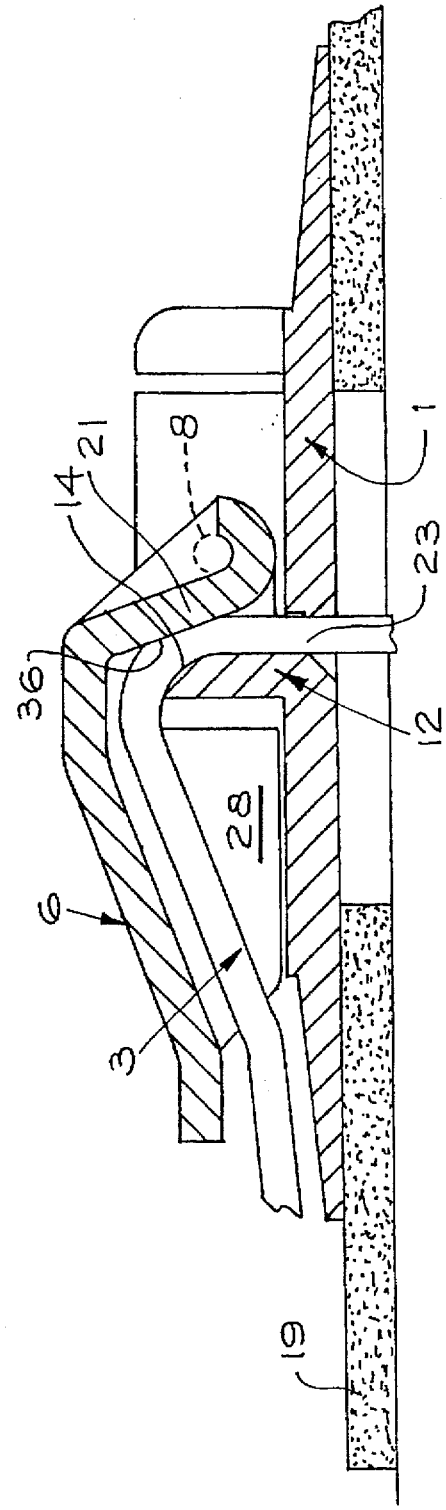

CATHETER CLAMP

BACKGROUND TO THE INVENTION

This invention relates to a clamp for attaching catheters to patients' skin at the insertion site.

Catheters can be inserted into patients where there is a requirement, for example, to administer continuous or repeated doses of analgesia, such as infusions for epidurals, spinals or nerve blocks, or to provide intravenous feed lines, chest drains etc.

Catheters are typically flexible tubes of small diameter which are difficult to hold and consequently easily pulled from the patient or the end displaced, thereby causing ineffective pain control when used to administer analgesia. Also flexure of the catheter can cause analgesia to leak back along the outside of the catheter.

Traditionally catheters have been either sutured to the patients skin, which is time consuming and distressing to the patient, or taped to the patients skin by various ad-hoc methods giving inconsistent results with high risk of catheter displacement and leakage. Also, as the catheter leaves the patient perpendicular to the surface of the skin it is necessary to bend the catheter through a right angle before being taped to the patient, so that kinking of the catheter can occur at the bend causing the catheter to occlude.

SUMMARY OF THE PRESENT INVENTION

According to the present invention there is provided a catheter clamp comprising a base adapted to be secured to the skin by adhesive means or by suture, an aperture in the base through which a catheter tube can be inserted, the tube in use extending substantially perpendicular to the skin, curved tube support means for supporting in use a curved portion of the tube which extends through an arc of substantially 90°, manually operable clamping means which is manually displaceable relative to the base from an inoperative position, in which movement of the tube passing through said aperture is substantially unrestricted by the clamping means, to an operative clamping position in which the tube is gripped between first and second clamping surfaces, one of said clamping surfaces being provided on the clamping means, and the other of said clamping surfaces being provided on an abutment which is fixed relative to the base.

The invention provides a device through which a catheter can be inserted and bent through a right angle without kinking. The device may be of a shape and size that can be secured to the skin by tape, sticky pad or suture.

In one preferred embodiment the manually operable clamping means comprises an arm pivotally mounted with respect to the base, and in another preferred embodiment the manually operable clamping means comprises a slider which is slidable relative to the base.

When the clamping means is an arm the arm is conveniently pivotally mounted between parallel side walls upstanding from the base, the arm preferably being housed substantially between the side walls in an operative clamping position of the arm.

Preferably the clamp comprises arm retention means adapted to hold the arm in a clamping position is comprised by co-operating formations provided on the arm and on said side walls.

Preferably the arm is of substantially channel section and is so arranged as in use to embrace the tube extending through said aperture as the arm is pivoted from an inoperative position towards an operative clamping position.

The curved tube support means is preferably provided on a post upstanding from the base, and preferably the post is formed with a channel the surface of which constitutes said other clamping surface, the channel extending substantially perpendicular to the base, and being contiguous with said curved support means which is also of channel section.

Preferably said one clamping surface on the arm is a curved camming surface which is eccentric to the axis of pivot, and is so arranged that in use as the arm is swung from an inoperative position towards an operative clamping position the camming surface exerts an increasing clamping force on the tube.

When the manually operable clamping means is a slider, the slider is preferably movable by finger pressure from an inoperative position to an operative clamping position in which the slider is held relative to the base by retention means.

The slider is preferably of substantially H-shape and the retention means is carried by ends of the limbs of the H-shape.

The curved tube support means is preferably provided on the slider.

The slider preferably carries additional tube clamping means spaced from the curved tube support means, the curved tube support means being adapted to support the tube when the tube is passed through the additional tube clamping means, said additional tube clamping means being so configured as to enable the tube to be snapped into position in the additional tube clamping means.

BRIEF DESCRIPTION OF THE DRAWINGS

Various catheter clamps in accordance with the invention will now be described, by way of example only, with reference to the accompanying drawings, in which:

FIGS. 6 and 7 are views similar to FIG. 3 but showing two modified clamps.

DETAILED DESCRIPTION OF THE PREFERRED EMBODIMENTS

For convenience, in the following description and claims the catheter clamps will be described as if the base plate is horizontal in use, but it will be appreciated that the base plate will not generally be horizontal in use.

Figure 1:
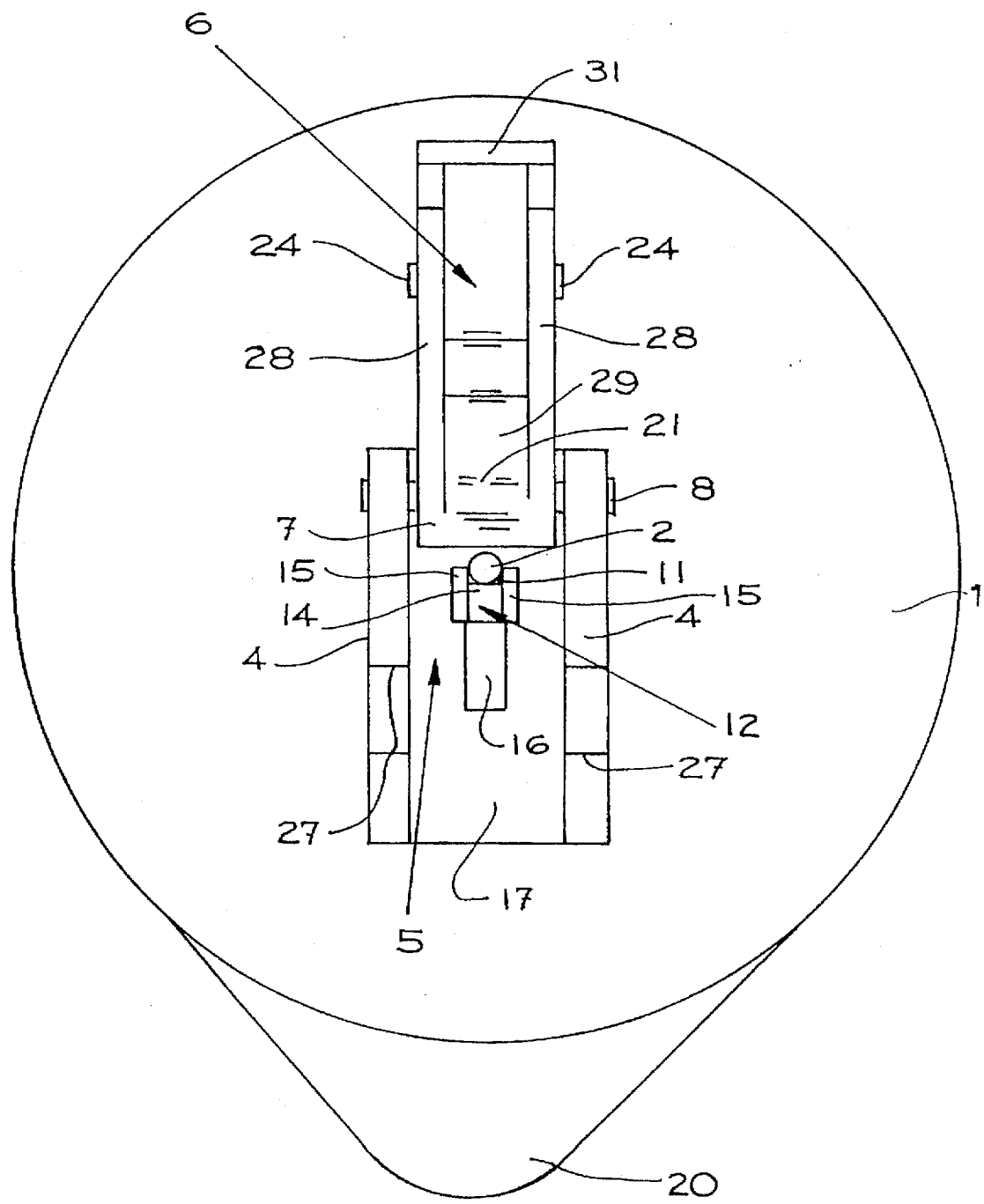
FIG. 1 is a plan view of a catheter clamp incorporating a pivoted clamp arm, the arm being shown in the fully open position.
Figure 2:
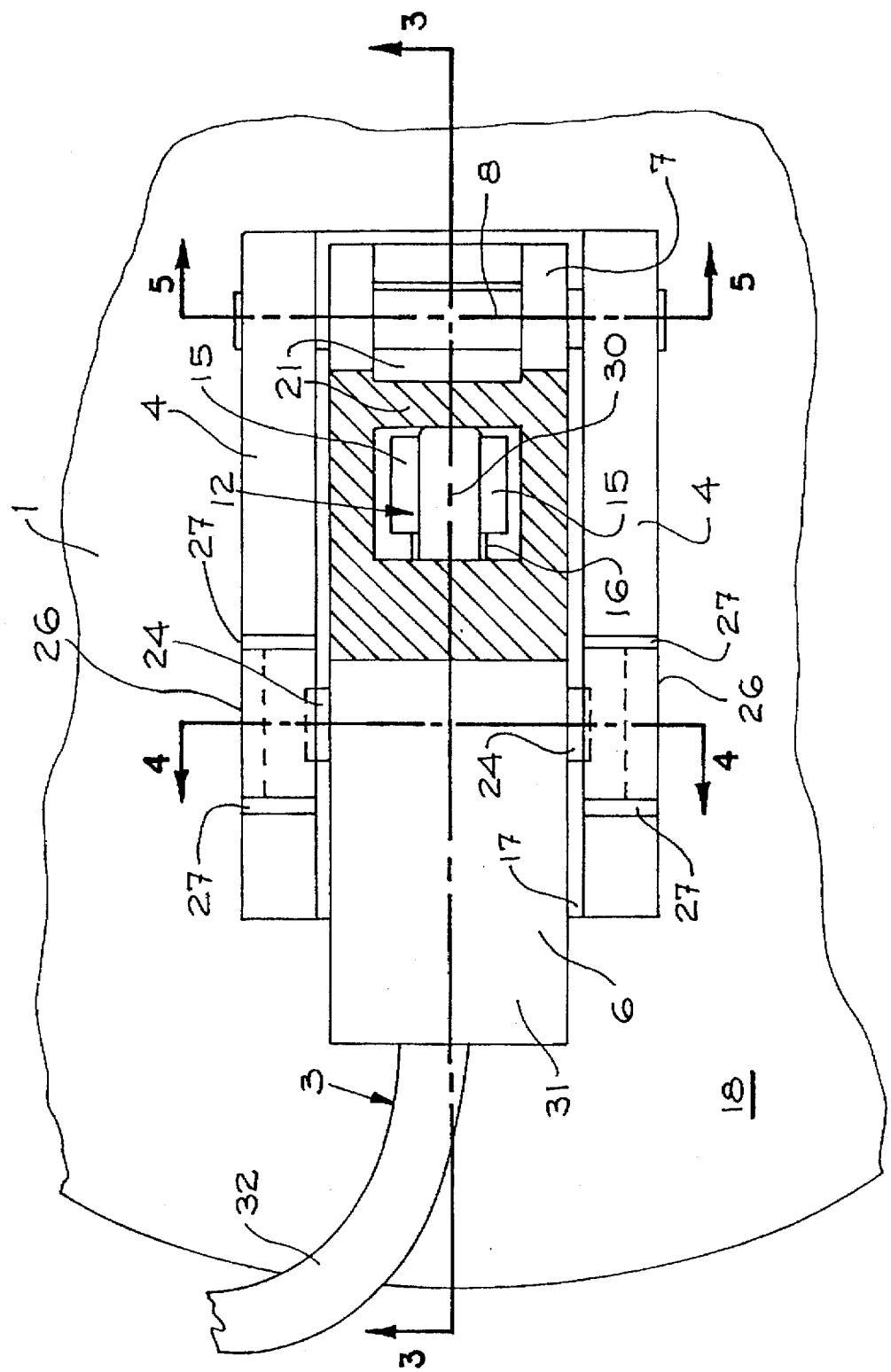
FIG. 2 is an enlarged plan view of the clamp of FIG. 1, with the arm sectioned on the line 2—2 of FIG. 3, and showing the arm in an operative position clamping a catheter tube.
Figure 3:
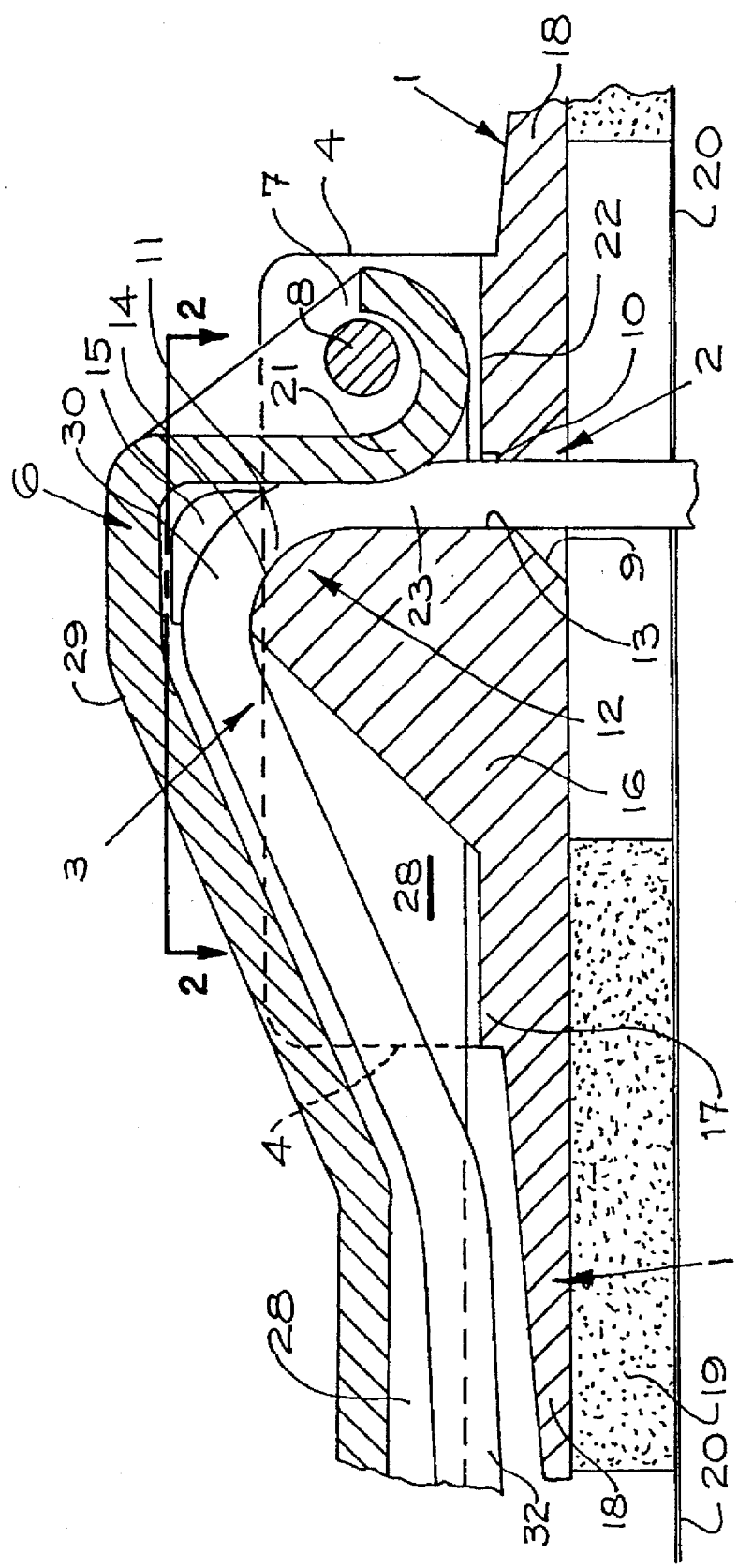
FIG. 3 is a vertical section on line 3—3 of FIG. 2.

Referring to FIGS. 1 to 3 the catheter clamp comprises a circular base plate 1 of substantially rigid plastics material, and is provided with a central hole 2 to receive a catheter tube 3, and formed integrally with a pair of upstanding, elongate parallel side walls 4 defining therebetween a channel 5 of rectangular transverse cross-section to accommodate a substantially rigid clamp arm 6. The clamp arm 6, which is manually operated, is pivoted at one end 7 thereof by a pivot pin 8 which is an interference fit in respective holes provided in walls 4.

As shown in the drawings, the axis of the pivot pin is close to but displaced from the hole 2 and the shape of the pivoted end 7 of the arm is such that when the arm is in a fully-open position, as in FIG. 1, the hole 2 is not obstructed by the arm, thereby enabling the catheter tube to be passed freely through the hole 2. The bore defining hole 2 is provided with a frusto-conical counterbore 9 to the underside of plate I to assist in initial insertion of the tube end, and the main part 10 of the bore is dimensioned to enable the tube to pass freely through the hole into the lower end of a close-fitting channel 11, FIG. 1, defined in an upstanding post 12.

Channel 11 is vertical at the lower end but the upper end thereof curves progressively away from the axis of pivot 8, thereby defining a vertical lower channel base portion 13 and an upper convex channel base portion 14 extending through an arc of substantially 80°. As shown in FIG. 3, the channel base portions 13 and 14 provide substantially rigid supporting surfaces for the tube when the arm 6 is in an operative clamping position. Parallel side walls of the post 12 which define the channel in the post are referenced 15 in FIGS. 1 to 3. An optional post-supporting buttress 16 is provided in this embodiment.

Base plate I has a thickened rectangular portion 17 extending beneath and between the side walls 4 to provide adequate strength to support the side walls 4. The outer annular portion 18 is of tapering radial cross-section. An annular sticky foam pad 19, with release paper 20, is provided on the underside of base plate I for adhesively securing the base plate I to the patient's skin.

The pad 19 may be of larger plan area than the base plate I (as in FIGS. 6 and 7), so as to increase the area of contact with the patient's skin.

The arm 6 comprises a tube-clamping portion 21 adapted to clamp the tube 3 into the lower portion of the channel 11 in the post 12, the tube-clamping portion 21 presenting a camming surface 22 extending eccentrically about the axis of pivot 8 and so arranged as to exert an increasing clamping force on the tube in the region 23 as the arm 6 is pivoted anti-clockwise in FIG. 3 towards the operative clamping position shown in FIG. 3.

The arm 6 is held in the operative clamping position by the engagement of a pair of projections 24 with respective downwardly facing abutments 25 provided on vertical spring arms 26 which are reduced thickness portions of the respective side walls 4, defined by pairs of vertical slots 27.

Figure 4:
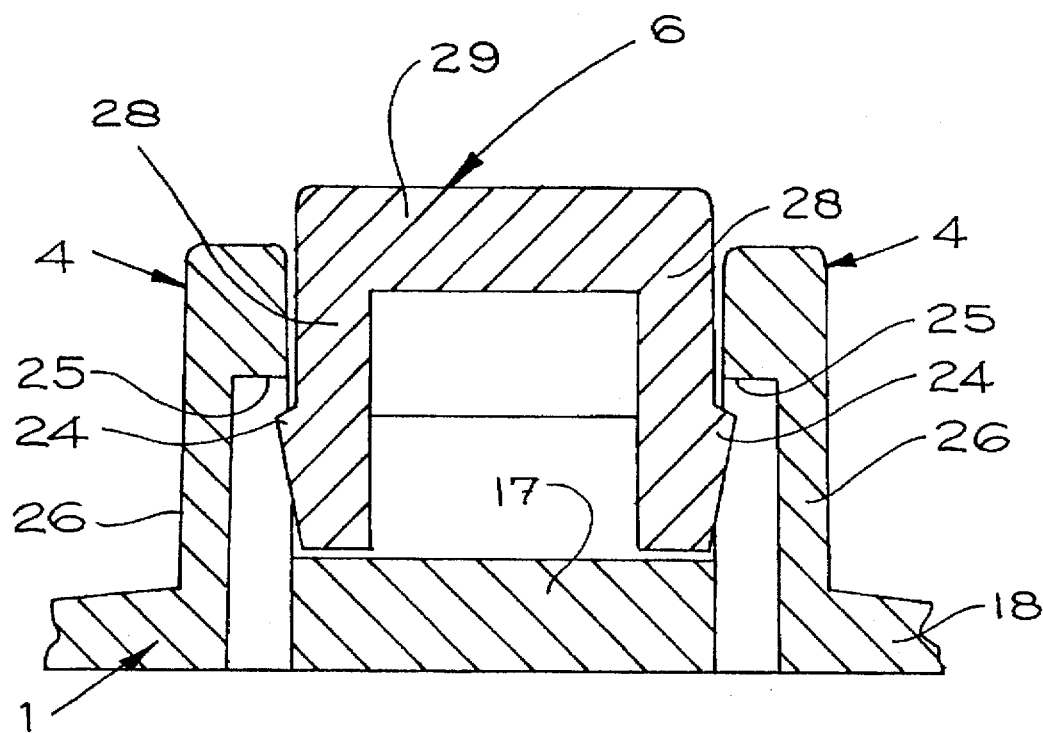
FIG. 4 is a section on the line 4—4 of FIG. 2.

Arm 6 is of generally channel section for most of the length thereof defined by parallel arm side walls 28, shown in FIG. 4, and by a top wall 29, the depth of the side walls 28 being greatest in the region of the post 12 (in the closed position of the arm) in order to accommodate the post 12, and the bent portion 30 of the tube 3, and said channel section is closed at the right-hand end in FIG. 3 by said tube clamping portion 21.

The channel section configuration of arm 6 helps to embrace the tube 3 as the arm is brought from the fully open condition of FIG. I, anti-clockwise in FIG. 3, to urge the tube against the post 12.

It will be appreciated that the curved portion 14 of the base of the channel in post 12 supports the tube against kinking. The camming action of the clamping portion 21 exerts a progressively increasing clamping action on tube portion 23 as the arm 6 is pivoted towards the clamping position of FIG. 3. The dimensions of the clamping portion 21, particularly the channel 11, are chosen so as to ensure that the tube portion is firmly clamped but avoiding significant constriction of the tube. In operation, the sides of the channel 11 hold the tube 3 secure and enable a substantial clamping force to be applied thereto.

Since the clamping portion 21 is positioned relatively close to the pivot 8, it will be appreciated that finger operation of the free end 31 of the arm 6 achieves a substantial mechanical advantage to provide an easy yet positive clamping action.

In use any pulling on the free end 32 of the tube will result in the curved tube portion 30 and clamped portion 23 being urged more firmly into the post channel, against surfaces 14 and 23 and sides of the channel 11, thereby increasing the resistance to the tube being pulled through hole 2.

Figure 5:
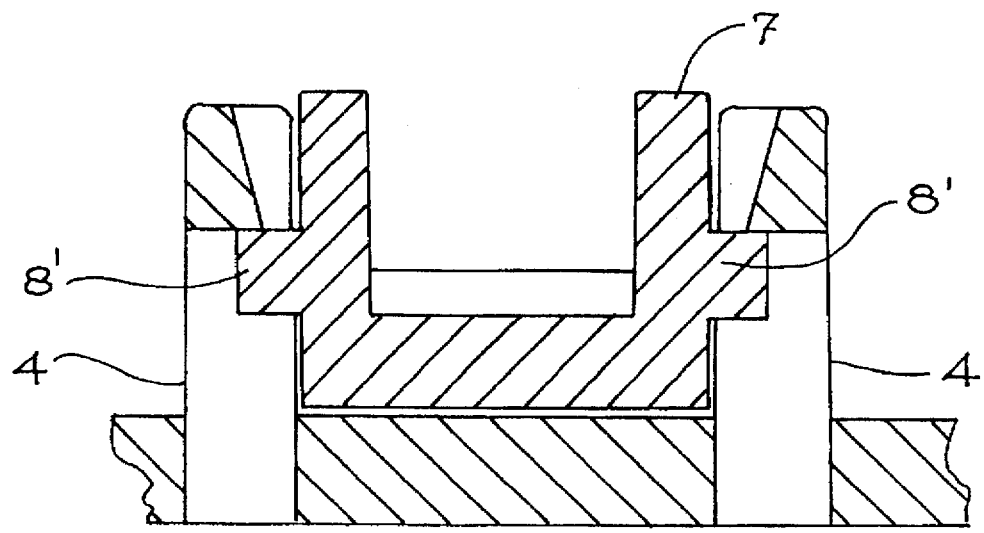
FIG. 5 is a section on the line 5—5 of FIG. 2 but of a modified clamp in which pivot trunnions are provided integrally on the arm, the trunnions being snap-engageable into position.

With reference to FIG. 5, this shows a modified pivot structure for the arm in the embodiment of FIGS. I to 4, the pivot pin 8 of that embodiment being replaced by trunnions $8^1$ provided integrally on the arm end 7, the side walls 4 being suitably relieved to provide a snap-engagement on assembly of the arm to the side walls 4.

In the modifications of FIGS. 6 and 7 parts corresponding to those of the embodiment of FIGS. I to 4 have been given corresponding reference numerals.

In the modification of FIGS. 6 and 7 the clamping portion 21 of the handle is not eccentric to the axis of the handle pivot 8. Instead, in FIG. 6 a flat surface 35 is provided on the part-circular arm surface 22 to allow the tube 3 to slide freely past the arm when the arm is in an open position. In FIG. 7 the arm is so shaped that inclined face 36 on the arm presses the tube against curved surface 14 when the arm is clipped in the clamping position. The adhesive pad 19 is of larger plan area than the base plate 1, so that it extends beyond the base-plate, and increases the area of contact with the patient's skin.

Figure 8:
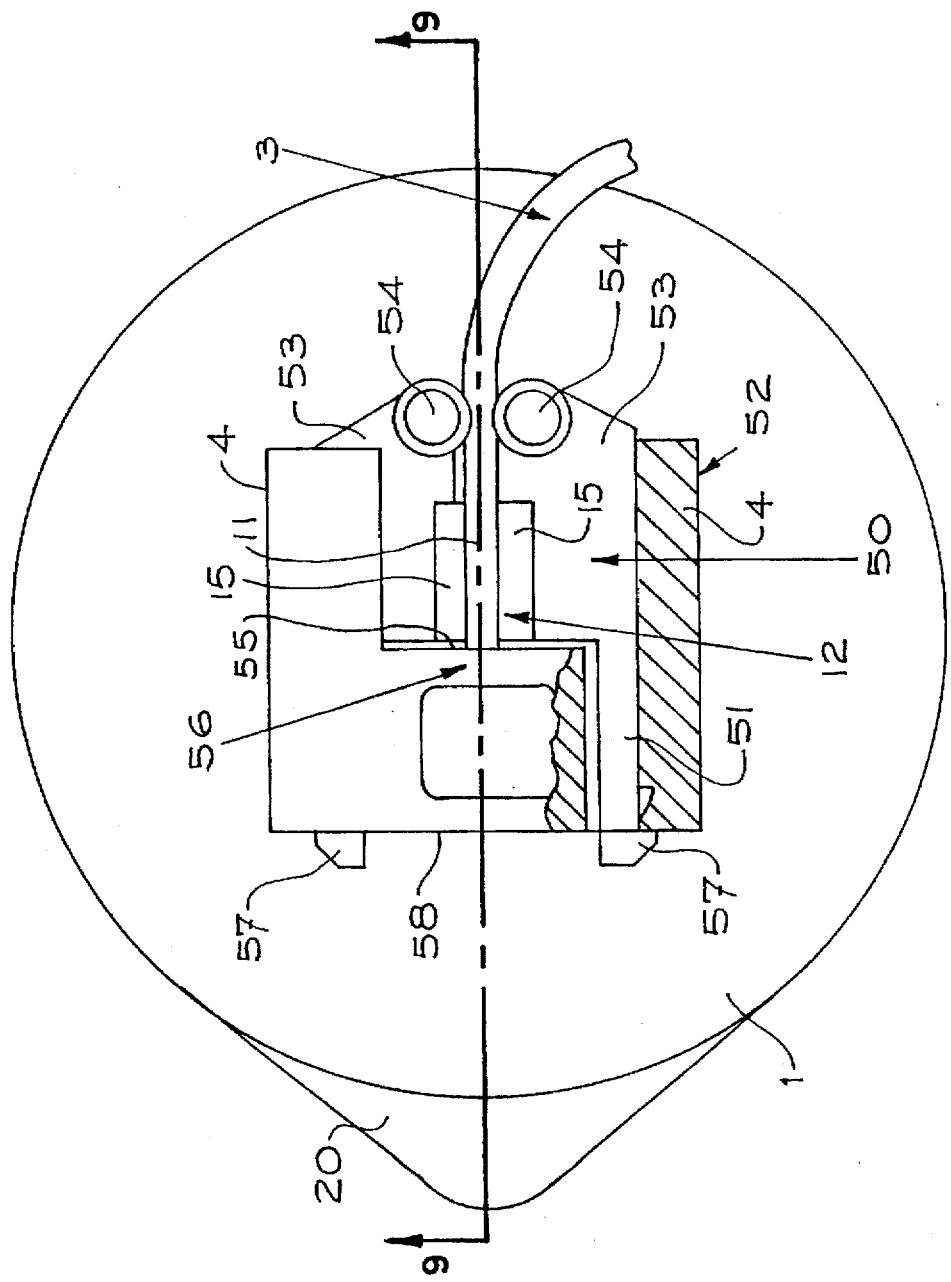
FIG. 8 is a plan view of a further catheter clamp, the clamp incorporating a slider, the slider being shown in an operative position clamping a catheter tube; and the body being partially sectioned on the line 8—8 of FIG. 9.
Figure 9:
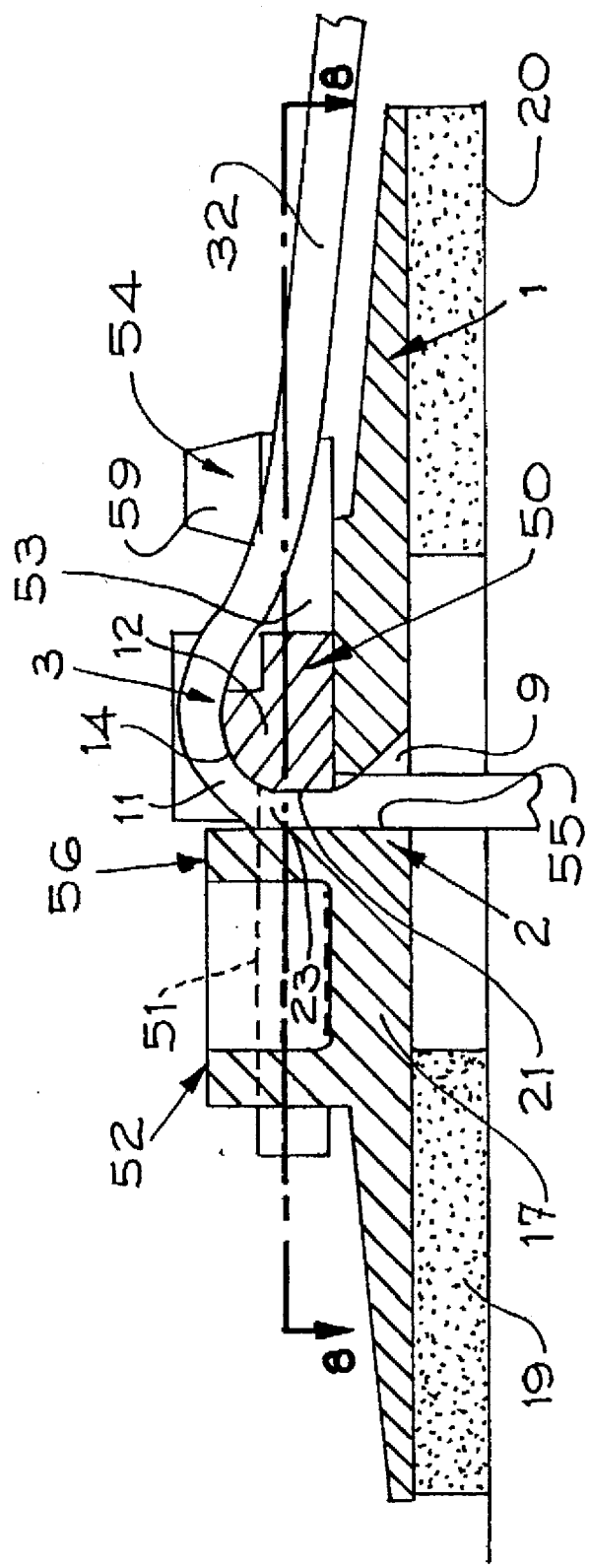
FIG. 9 is a vertical section on the line 9—9 of FIG. 8.

In FIGS. 8 and 9 parts corresponding to those of the clamp of FIGS. 1 to 4 have been given corresponding reference numerals. In this embodiment the post 12 is an integral upstanding portion of a slider 50 which is horizontally slidable relative to the base plate I in grooves in the body 52, the slider being slidably guided between parallel side walls 4 of the body. As viewed in plan, the slider 50 is of substantially H-shape, the bridging portion of the H being constituted by the base of post 12, one pair of limbs of the H being constituted by parallel locking pins 51, and the other pair of limbs by legs 53 which carry respective waisted retention pins 54.

A vertical abutment wall 55 is provided on an upstanding body block 56 integral with base 1, the wall 55 confronting the post 12 whereby when the slider is urged to the left in FIG. 9 against a tube 3 that has been inserted through hole 2, the portion 23 of the tube above hole 2 is clamped between abutment wall 55 and surfaces 14 and 21 of a curved channel-section formation provided in the post 12.

The slider 50 is retained in this clamping position by the engagement of laterally projecting abutments 57 on the free ends of limbs 51 with the end face 58 of block 56.

Once the slider 50 has been brought to the clamping position of FIG. 9, the free end of the tube 32 is manipulated to bend the tube portion 11 over the curved surface 14 of the post, and the tube is snapped into position between the waisted portions of pins 54, as shown in FIGS. 8 and 9, thereby to retain the tube portion 11 in a smoothly curved condition, the pins 54 also gripping the tube. The frusto-conical upper portions 59 of the pins assist in guiding the tube downwards into the waisted portions.

Any pulling on the free end 32 of the tube in use will be resisted by the clamping force from pins 54, and curved portion 11 is urged more firmly against the curved surfaces 14 thereby increasing the resistance to the tube being pulled through hole 2.

It will be appreciated that the slider 50 is preferably constructed so as to be slidable by finger pressure alone from the inoperative position to clamping position.

I claim:

1. A catheter clamp comprising a base adapted to be secured to the skin, an aperture in the base through which a catheter tube can be inserted, curved tube support means for supporting in use a curved portion of the tube with said tube support means having a passageway whose longitudinal center extends through an arc, manually operable clamping means which is manually displaceable relative to the base from an inoperative position, in which movement of the tube passing through said aperture is substantially unrestricted by the clamping means, to an operative clamping position in which the tube is gripped between first and second clamping surfaces and with at least one of the surfaces curved along a longitudinal direction of the passageway, one of said clamping surfaces being provided on the clamping means, and the other of said clamping surfaces being provided on an abutment which is fixed relative to the base.

2. A catheter clamp as claimed in claim 1 in which said manually operable clamping means comprises an arm pivotally mounted with respect to said base.

3. A catheter clamp as claimed in claim 1 provided with parallel sidewalls upstanding from said base, wherein the manually operable clamping means comprise an arm pivotally mounted between said parallel sidewalls.

4. A catheter clamp as claimed in claim 3 provided with arm retention means adapted to hold the arm in a clamping position, said arm retention means comprising co-operating formations provided on said arm and on said sidewalls.

5. A catheter clamp as claimed in claim 1 in which said manually operable clamping means comprise an arm of substantially channel section pivotally mounted with respect to said base and operable so as to embrace the tube extending through said aperture as said arm is pivoted from an inoperative position towards an operative clamping position.

6. A catheter clamp as claimed in claim 1 provided with a post upstanding from the base, said curved tube support means comprising said post.

7. A catheter clamp as claimed in claim 6 in which said post is formed with a channel, the surface of which constitutes said other of said clamping surfaces, the channel extending substantially perpendicular to said base, and contiguous with said curved support means, said curved support means also being of channel section.

8. A catheter clamp as claimed in claim 1 wherein said manually operable clamping means comprise an arm pivotally mounted with respect to said base, and wherein said one clamping surface on said arm comprises a curved camming surface which is eccentric to the axis of the pivot mounting of said arm and is operable so that, in use, as the arm is swung from an inoperative position towards an operative clamping position said camming surface exerts an increasing clamping force on said tube.

9. A catheter clamp as claimed in claim 1 in which said manually operable clamping means comprises a slider which is slidable relative to said base.

10. A catheter clamp as claimed in claim 9 in which said slider is movable by finger pressure from an inoperative position to an operative tube clamping position, and slider retention means operable to hold said slider in place.

11. A catheter clamp as claimed in claim 1 wherein said manually operable clamping means comprises a slider slidable relative to said base, and slider retention means operable to hold said slider in place, said slider being of substantially H-shape, said slider retention means being carried by ends of the limbs of the H-shaped slider.

12. A catheter clamp as claimed in claim 1 in which said manually operable clamping means comprises a slider which is slidable relative to said base, said curved tube support means being mounted on the slider.

13. A catheter clamp as claimed in claim 12 in which the slider carries additional tube clamping means spaced from the curved tube support means, the curved tube support means being adapted to support the tube when the tube is passed through the additional tube clamping means, said additional tube clamping means being so configured as to enable the tube to be snapped into position in the additional tube clamping means.

14. A catheter clamp as claimed in claim 1 wherein the base is of substantially rigid construction.

15. A catheter clamp as claimed in claim 1 wherein the clamping means are of substantially rigid construction.

16. A catheter clamp as claimed in claim 1 wherein the base is provided with an adhesive pad whereby the base may be secured to the skin.

17. A catheter clamp as claimed in claim 16 wherein the pad has a larger plan area than the base.

18. The catheter clamp as defined in claim 1 wherein the curved tube support means extends through an arc of about 80° to 90°.

19. The catheter clamp as defined in claim 1 wherein the base is secured to the skin by at least one of an adhesive strip and a suture.

20. A catheter clamp including a base housing to be secured to a patient's skin, comprising:

an aperture having a center line longitudinal aperture axis in said base housing through which a catheter tube can be inserted;

a curved support structure smoothly curved along a longitudinal axis of a passageway to support the catheter tube passing through the aperture in said base, said curved support structure longitudinal axis diverging from the center line longitudinal aperture axis; and manually operable clamping means which is displaceable relative to said base housing and when engaged to the catheter tube the tube is gripped between a first and a second clamping surface, said first clamping surface being provided on said clamping means and said second clamping surface being provided on an abutment fixed relative to said base housing.

* * * * *